(12) United States Patent
Singh et al.

(10) Patent No.: US 6,541,515 B2
(45) Date of Patent: Apr. 1, 2003

(54) HIV INTEGRASE INHIBITORS

(75) Inventors: Sheo Bux Singh, Edison, NJ (US); Hiranthi Jayasuriya, Edison, NJ (US); Ziqiang Guan, Edison, NJ (US); Keith C. Silverman, Somerset, NJ (US); Russell B. Lingham, Watchung, NJ (US); Anne W. Dombrowski, East Brunswick, NJ (US); Daria J. Hazuda, Doylestown, PA (US); Jon D. Polishook, Cranford, NJ (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 09/925,114

(22) Filed: Aug. 9, 2001

(65) Prior Publication Data

US 2002/0045658 A1 Apr. 18, 2002

Related U.S. Application Data

(60) Provisional application No. 60/224,117, filed on Aug. 9, 2000.

(51) Int. Cl.$^7$ ............... A61K 31/215; A61K 31/19; C07C 69/75; C07C 61/28
(52) U.S. Cl. ............... 514/510; 514/529; 514/557; 514/561; 560/119; 562/501
(58) Field of Search ............... 560/119, 118, 560/126, 128; 562/500, 501; 514/510, 506, 557, 561, 529

(56) References Cited

U.S. PATENT DOCUMENTS

| | | | |
|---|---|---|---|
| 4,438,277 A | * 3/1984 | Terahara et al. | 560/119 |
| 4,719,229 A | * 1/1988 | Reamer et al. | 514/460 |
| 5,116,870 A | * 5/1992 | Smith et al. | 514/548 |
| 5,256,811 A | * 10/1993 | Todd et al. | 560/10 |
| 5,276,055 A | 1/1994 | Cabello et al. | |
| 5,276,177 A | * 1/1994 | Yoshida et al. | 562/501 |
| 5,304,485 A | 4/1994 | Bills et al. | |
| 5,441,987 A | 8/1995 | Harris et al. | |
| 5,449,684 A | * 9/1995 | Tanaka et al. | 514/452 |

OTHER PUBLICATIONS

L. Ratner et al., "Complete Nucleotide sequence of the AIDS virus, HTLV–III", Nature, vol. 313, pp. 277–284 (Jan. 24, 1985).
H. Toh et al., "Close structural resemblance between putative polymerase of a Drosophila transposable genetic element 17.6 and pol gene product of Moloney murine leukaemia virus", The EMBO Journal, vol. 4, No. 5, pp. 1267–1272 (1985).
M. D. Power et al., "Nucleotide Sequence of SRV–1, Type D Simian Acquired Immune Deficiency Syndrome Retrovirus", Science, vol. 231, pp. 1567–1572 (1986).
L. H. Pearl et al., "A structural model for the retroviral proteases", Nature, vol. 329, pp. 351–354 (Sep. 24, 1987).
O. D. Hensens et al., "Structure Elucidation of Australifungin, a Potent Inhibitor of Sphinganine N–Acyltransferase in Sphingolipid Biosynthesis from *Sporormiella australis*", J. Org. Chem., vol. 60, No. 6, pp. 1772–1776 (1995).

\* cited by examiner

Primary Examiner—Jean F. Vollano
(74) Attorney, Agent, or Firm—Kenneth R. Walton; Melvin Winokur

(57) ABSTRACT

Compounds useful in the inhibition of HIV integrase, the prevention or treatment of infection by HIV and the treatment of AIDS, either as compounds, pharmaceutically acceptable salts, pharmaceutical composition ingredients, whether or not in combination with other antivirals, immunomodulators, antibiotics or vaccines are described. Methods of treating AIDS and methods of preventing or treating infection by HIV are also described. The culture Cytospora sp. MF 6608 (ATCC PTA-1691) is also disclosed, as well as processes for making a compound of the present invention employing the culture.

15 Claims, No Drawings

HIV INTEGRASE INHIBITORS

CROSS-REFERENCE TO RELATED APPLICATIONS

This application claims the benefit of U.S. Provisional Application No. 60/224,117 filed Aug. 9, 2000, the disclosure of which is hereby incorporated by reference in its entirety.

FIELD OF THE INVENTION

The present invention relates to certain compounds, pharmaceutical compositions containing the compounds, and the microbial production of the compounds. The compounds are useful as HIV integrase inhibitors.

References are made throughout this application to various published documents in order to more fully describe the state of the art to which this invention pertains. The disclosures of these references are hereby incorporated by reference in their entireties.

BACKGROUND OF THE INVENTION

A retrovirus designated human immunodeficiency virus (HIV) is the etiological agent of the complex disease that includes progressive destruction of the immune system (acquired immune deficiency syndrome; AIDS) and degeneration of the central and peripheral nervous system. This virus was previously known as LAV, HTLV-III, or ARV. A common feature of retrovirus replication is the insertion by virally-encoded integrase of proviral DNA into the host cell genome, a required step in HIV replication in human T-lymphoid and monocytoid cells. Integration is believed to be mediated by integrase in three steps: assembly of a stable nucleoprotein complex with viral DNA sequences; cleavage of two nucleotides from the 3' termini of the linear proviral DNA; covalent joining of the recessed 3' OH termini of the proviral DNA at a staggered cut made at the host target site. The fourth step in the process, repair synthesis of the resultant gap, may be accomplished by cellular enzymes.

Nucleotide sequencing of HIV shows the presence of a pol gene in one open reading frame (Ratner et al., *Nature* 1985, 313: 277). Amino acid sequence homology provides evidence that the pol sequence encodes reverse transcriptase, integrase and an HIV protease (Toh et al., *EMBO J.* 1985, 4: 1267; Power et al., *Science* 1986, 231: 1567; Pearl et al., *Nature* 1987 329: 351). All three enzymes have been shown to be essential for the replication of HIV.

It is known that some antiviral compounds which act as inhibitors of HIV replication are effective agents in the treatment of AIDS and similar diseases, e.g., azidothymidine or AZT. Applicants demonstrate that the compounds of this invention are inhibitors of HIV integrase. The applicants additionally demonstrate that inhibition of integrase in vitro is a direct result of inhibiting the strand transfer reaction catalyzed by the recombinant integrase in vitro. The particular advantage of the present invention is highly specific inhibition of HIV integrase and HIV replication. The compounds of the present invention inhibit integrases of closely related lentiviruses such as HIV 2 and SIV, but not integrases from more distantly related retroviruses, for example RSV. These compounds do not inhibit binding or catalysis of other nucleic acid binding proteins, including enzymatic reactions such as those catalyzed by HIV reverse transcriptase, HIV Rnase H, Influenza transcriptase, Hepatitis C polymerase, Yeast DNA polymerase, DNase I, Eco RI endonuclease, or mammalian polymerase II.

Hensens et al., *J. Org. Chem.* 1995, 60: 1772–1776, discloses australifungin and australifunginol. U.S. Pat. No. 5,276,055 discloses australifungin and related compounds, and their use as antifungal agents. U.S. Pat. No. 5,304,485 discloses *Sporormiella australis* (MF5672, ATCC 74157) and its cultivation in a suitable nutrient medium for the provision of australifungin. U.S. Pat. No. 5,441,987 discloses australifunginol and its use as an antifungal agent.

SUMMARY OF THE INVENTION

Applicants have discovered that certain novel compounds are potent inhibitors of HIV integrase. These compounds are useful for the treatment of HIV infection or AIDS. More particularly, the present invention includes compounds of Formula (I):

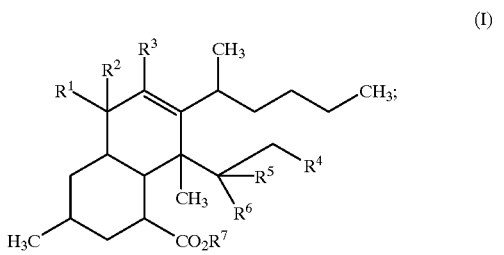

wherein
one of $R^1$ and $R^2$ is —H, and the other of $R^1$ and $R^2$ is —OH; or $R^1$ and $R^2$ together form oxo;
$R^3$ is —OH, —OC(O)CH$_3$ or —OR$^a$;
$R^4$ is —CH$_2$OH, —CH$_2$OC(O)CH$_3$, —CHO, or —CO$_2$H;
one of $R^5$ and $R^6$ is —H, and the other of $R^5$ and $R^6$ is —OH; or $R^5$ and $R^6$ together form oxo;
$R^7$ is —H, —R$^a$, —NH$_2$, or —NR$^a$R$^b$;
each $R^a$ is independently —C$_1$–C$_4$ alkyl; and
$R^b$ is —H or —C$_1$–C$_4$ alkyl;
or a pharmaceutically acceptable salt thereof.

The present invention also includes use of these compounds in the inhibition of HIV integrase, the prevention of infection by HIV, the treatment of infection by HIV, and the treatment of AIDS and/or ARC, wherein the compounds are used per se or as their pharmaceutically acceptable salts or hydrates (when appropriate), either alone or as ingredients in pharmaceutical compositions, optionally in combination with other antivirals, anti-infectives, immunomodulators, antibiotics or vaccines. The present invention further includes the culture Cytospora sp. MF 6608 (ATCC PTA-1691) and processes for making Compound A (described below) of the present invention employing the culture.

These and other embodiments, aspects and features of the present invention are either further described in or will be apparent from the ensuing description, examples, and appended claims.

DETAILED DESCRIPTION OF THE INVENTION

The present invention includes compounds of Formula (I) as described above. These compounds and their pharmaceutically acceptable salts are useful as HIV integrase inhibitors. One embodiment of the present invention is a compound of Formula (II):

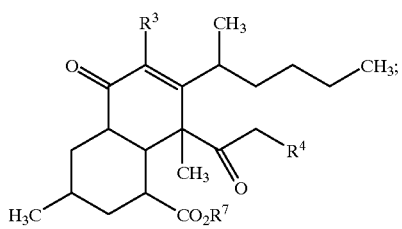

(II)

wherein $R^3$, $R^4$ and $R^7$ are defined above;
or a pharmaceutically acceptable salt thereof An aspect of the preceeding embodiment is a compound of formula (II), wherein $R^3$ is —OH, and $R^4$ is —CH$_2$OH, or a pharmaceutically acceptable salt thereof.

Another embodiment of the present invention is Compound A, which is a compound of formula:

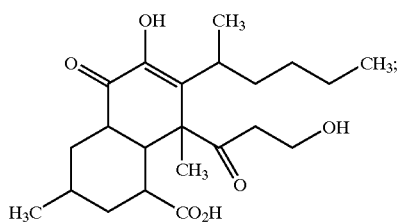

A or a pharmaceutically acceptable salt thereof.

The present invention also includes pharmaceutical compositions which comprise a therapeutically effective amount of a compound of the present invention, or a pharmaceutically acceptable salt thereof, and a pharmaceutically acceptable carrier. These pharmaceutical compositions are useful for inhibiting HIV integrase, for treating infection by HIV, or for treating AIDS or ARC. In one embodiment, the pharmaceutical composition comprises a compound of Formula (II), or a pharmaceutically acceptable salt thereof, and a pharmaceutically acceptable carrier. In another embodiment, the pharmaceutical composition comprises Compound A, or a pharmaceutically acceptable salt thereof, and a pharmaceutically acceptable carrier. In still another embodiment, the pharmaceutical composition further comprises a therapeutically effective amount of an agent for treating HIV infection or AIDS selected from (a) an HIV/AIDS antiviral agent, (b) an immunomodulator, and (c) an anti-infective agent (all described below). A class of this embodiment is the pharmaceutical composition which includes an HIV/AIDS antiviral agent, such as indinavir or a pharmaceutically acceptable salt thereof.

The present invention also includes pharmaceutical compositions which comprise a combination of a therapeutically effective amount of a compound of Formula (I), or a pharmaceutically acceptable salt thereof, and a therapeutically effective amount of an agent for treating HIV infection or AIDS selected from (a) an HIV/AIDS antiviral agent, (b) an immunomodulator, and (c) an anti-infective agent. In one embodiment, the compound employed in the combination is a compound of Formula (II) or a pharmaceutically acceptable salt thereof. In another embodiment, the compound employed in the combination is Compound A or a pharmaceutically acceptable salt thereof.

The present invention also includes pharmaceutical compositions made by combining a compound of Formula (I) (or a compound of Formula (II) or Compound A), or a pharmaceutically acceptable salt thereof, and a pharmaceutically acceptable carrier. The present invention also includes a process for making pharmaceutical compositions which comprises combining a compound of Formula (I) (or a compound of Formula (II) or Compound A), or a pharmaceutically acceptable salt thereof, and a pharmaceutically acceptable carrier.

The present invention also includes methods of inhibiting HIV integrase, of treating infection by HIV, and of treating AIDS or ARC, wherein the methods comprise administering to a mammal in need of such inhibition or treatment a therapeutically effective amount of a compound of Formula (I), or a pharmaceutically acceptable salt thereof, optionally in combination with a therapeutically effective amount of another agent for treating HIV infection or AIDS selected from (a) an HIV/AIDS antiviral agent (e.g., indinavir or one of its pharmaceutically acceptable salts), (b) an immunomodulator, and (c) an anti-infective agent. Also included in the present invention are methods of inhibiting HIV integrase, of treating infection by HIV, and of treating AIDS or ARC, by administering to a mammal in need thereof one of the pharmaceutical compositions as heretofore described. In embodiments of these methods, the compound is a compound of Formula (II) or is Compound A.

The present invention also includes a culture of Cytospora sp. MF 6608 (ATCC PTA-1691), which can be used to form Compound A:

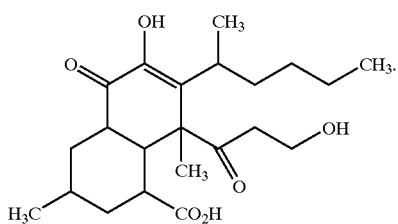

A

Compound A can be isolated from the aerobic fermentation of a culture of M 6608 (ATCC PTA-1691). A culture of MF 6608 (ATCC PTA-1691) is defined as substantially free of its natural soil contaminants and capable of forming Compound A in a recoverable amount. The culture should be free from viable contaminating microorganisms deleterious to the production of Compound A. A biologically pure culture of MF 6608 (ATCC PTA-1691) may also be employed. In one embodiment, the present invention includes a culture of MF 6608 (optionally biologically pure), or a mutant thereof, capable of producing Compound A in a recoverable amount.

Suitable mutant strains of MF 6608 can be obtained by chemically induced mutagenesis using mutagens such as nitrosoguanidine, 1-methyl-3-nitro-1-nitrosoguanidine, ethyl methane sulfonate, 2-aminopurine, and the like. Mutant strains can also be obtained by radiation-induced mutagenesis, such as by irradiation with ultraviolet light (e.g., using a germicidal lamp), X-rays, or gamma rays (e.g., using a cobalt-60 source). Recombinant DNA techniques such as protoplast fusion, plasmid incorporation, gene transfer and the like may also be employed. Further description of mutagenic techniques can be found in Vinci and Bing, "Strain Improvement by Nonrecombinant Methods", in *Manual of Industrial Microbiology and Biotechnology* 1999, 2d edition, edited by Demain et al., ASM Press, 103–113; and in Carlton and Brown, "Gene Mutation", Chapter 13 in *Manual of Methods for General Bacteriology* 1985, edited by Gerhardt et al., ASM Press, 222–229.

The present invention also includes a process for making Compound A, which comprises cultivating Cytospora sp.

MF 6608 (ATCC PTA-1691) or a mutant thereof under conditions suitable for formation of the compound and recovering the compound. In one aspect the process comprises:

(a) fermenting a culture of Cytospora sp. MF 6608 (ATCC PTA-1691) or a mutant thereof to produce a fermentation broth;

(b) extracting the fermentation broth with an organic solvent; and (c) isolating Compound A.

Organic solvents suitable for extraction of the fermentation broth include methyl ethyl ketone, ethyl acetate, methylene chloride and chloroform.

Compound A can be isolated from the solvent extract by solvent partitioning and crystallization or by preparative HPLC on reversed phase systems.

The present invention also includes the use of a compound of Formula (I) or a pharmaceutical composition as described above or any of the above-described embodiments of the compound or pharmaceutical composition, in the preparation of a medicament for (a) inhibiting HIV integrase, (b) treating infection by HIV, or (c) treating AIDS or ARC.

The compounds of the present invention may have asymmetric centers and may occur, except when specifically noted, as mixtures of stereoisomers or as individual diastereomers, or enantiomers, with all isomeric forms being included in the present invention.

The variable $R^a$ can occur more than one time in a compound of Formula (I). Its definition on each occurrence is independent of its definition at every other occurrence. Combinations of substituents and/or variables are permissible only if such combinations result in stable compounds.

The present invention includes within its scope prodrugs of the compounds of this invention. In general, such prodrugs will be functional derivatives of the compounds of this invention which are readily convertible in vivo into the required compound. Thus, in the methods of treatment of the present invention, the term "administering" (defined below) shall encompass the treatment of the various conditions described with the compound specifically disclosed or with a compound which may not be specifically disclosed, but which converts to the specified compound in vivo after administration to the patient. Conventional procedures for the selection and preparation of suitable prodrug derivatives are described, for example, in *Design of Prodrugs* 1985, edited by H. Bundgaard, Elsevier.

The compounds of the present inventions are useful in the inhibition of HIV integrase, the prevention or treatment of infection by human immunodeficiency virus (HIV) and the treatment of consequent pathological conditions such as AIDS. Treating AIDS or preventing or treating infection by HIV is defined as including, but not limited to, treating a wide range of states of HIV infection: AIDS, ARC (AIDS related complex), both symptomatic and asymptomatic, and actual or potential exposure to HIV. For example, the compounds of this invention are useful in treating infection by HIV after suspected past exposure to HIV by e.g., blood transfusion, exchange of body fluids, bites, accidental needle stick, or exposure to patient blood during surgery.

The compounds of this invention are useful in the preparation and execution of screening assays for antiviral compounds. For example, the compounds of this invention are useful for isolating enzyme mutants, which are excellent screening tools for more powerful antiviral compounds. Furthermore, the compounds of this invention are useful in establishing or determining the binding site of other antivirals to HIV integrase, e.g., by competitive inhibition. Thus, the compounds of this invention are commercial products to be sold for these purposes.

Compound A can be prepared by an aerobic fermentation procedure employing MF 6608, as described below. Compound A can also be prepared by analogous fermentation procedures using mutants of MF 6608. Other compounds of Formula (I) can be prepared by chemical modification of Compound A.

ATCC Deposit of MF 6608 (ATCC PTA-1691), Identified as Cytospora sp.

A sample of MF 6608 (ATCC PTA-1691) was deposited at the American Type Culture Collection (ATCC), 10801 University Boulevard, Manassas, Va. 20110-2209 on Apr. 13, 2000. The culture access designation is PTA-1691. This deposit will be maintained in the ATCC for at least 30 years and will be made available to the public upon the grant of a patent disclosing it. It is understood that the availability of a deposit does not constitute a license to practice the subject invention in derogation of patent rights granted by government action.

General Characteristics and Description of MF 6608 (ATCC PTA-1691)

MF 6608 was isolated from leaf litter of *Manilkara bidentata* collected in Puerto Rico based on the particle-filtration isolation method described in Polishook et al., *J. Industrial Microbio.* 1996, 17: 284–294. MF 6608 has been identified as the fungus known as Cytospora sp., a coelomycete. Coelomycetes are described in Sutton, The Coelomycetes, 1980, Commonwealth Mycological Institute, Kew, Surrey, England.

In the following description, all capitalized color names are from Ridgway, Color Standards and Color Nomenclature, 1912, published by the author, Washington DC, 43 p.+53 pl. Unless otherwise indicated, the description of all growth conditions was after 10 days at 23° C. and 67% relative humidity in a 12 hour photoperiod under fluorescent light.

On oatmeal agar (Difco) colony, attaining radial growth of 61 mm. Culture mat from colony midpoint to margin cottony to thick cottony, white. From inoculation point to midpoint abundant black conidiomata underneath slightly matted aerial mycelium, white with light brown (Ochraceous Buff) patches sometimes extending to outer portions of culture mat. Margin entire, white. Soluble pigment, exudate and reverse absent.

On YME (yeast extract, 4.0 g; malt extract, 10.0 g; dextrose, 4.0 g; agar, 20 g; distilled water, 1 L) attaining a radial growth of 35 mm. Culture mat cottony, dull (brownish) white, coarse texture. At mid-point of culture, light brown (Cinnamon-Buff) area. Margin white, entire. Soluble pigment and exudate absent. Reverse yellow-brown (Raw Sienna) to yellow-orange (Light Orange-Yellow). Conidiomata production restricted to inoculation plug (PCA). At 37° C., in the dark with no humidity control, growth is limited to the inoculation plug.

On Potato-Carrot Agar (PCA) (Mycology Guidebook, 1981, R. Stevens (ed.), Univ. Wash. Press, Seattle, p.661) attaining a radial growth of 51 mm. Culture mat cottony, dull white, thicker towards margin. Soluble pigment and reverse absent. Exudate clear, limited to middle of colony. Margin entire, hyaline. Moderate black (mature, conidial mass) to brown (immature) conidiomata from inoculation point to middle part of colony.

On cornmeal agar (Difco), attaining a radial growth of 32 mm. Culture mat mostly appressed, with sparse, white aerial mycelium. Exudate, soluble pigment and reverse absent. Conidiomata production restricted to (PCA) inoculation plug.

Microscopic: Conidiomata olivaceous to black, irregularly shaped, typically 1.0–1.5 mm thick, multiloculed, mature conidia oozing from ostiole as clear to whitish mass. Conidiophores irregularly branched at base, forming a continuous hymenial layer, hyaline, smooth walled, septate, 10–15×1–2 μm. Conidiogenous cells phialidic, hyaline, smooth walled, thickened collarette. Conidia hyaline, 1-celled, smooth walled, allantoid, eguttulate, 4–6×1–2 μm.

In general, MF 6608 (ATCC PTA-1691) is strain cultured on a solid medium, or in an aqueous nutrient medium containing sources of assimilable carbon and nitrogen. For example, the cultures can be grown under submerged aerobic conditions (e.g., shaking culture, submerged culture, etc.) The aqueous medium is preferably maintained at a pH in the range of from about 6 to about 8 at the initiation of the fermentation process. The desired pH may be maintained by the use of a buffer such as morpholinoethane-sulfonic acid (MES), morpholinopropanesulfonic acid (MOPS), and the like, or by choice of nutrient materials which inherently possess buffering properties.

The preferred sources of carbon in the nutrient medium are carbohydrates such as glucose, fructose, xylose, galactose, glycerin, starch, sucrose, dextrin, and the like. Other sources which may be included are maltose, rhamnose, raffinose, arabinose, mannose, sodium succinate, and the like.

The preferred sources of nitrogen are yeast extract, meat extract, peptone, gluten meal, cottonseed meal, soybean meal and other vegetable meals (partially or totally defatted), casein hydrolysates, soybean hydrolysates, and yeast hydrolysates, corn steep liquor, dried yeast, wheat germ, feather meal, peanut powder, distiller's solubles, etc., as well as inorganic and organic nitrogen compounds such as nitrates, ammonium salts (e.g., ammonium nitrate, ammonium sulfate, ammonium phosphate, etc.), urea, amino acids, and the like.

The carbon and nitrogen sources, though advantageously employed in combination, need not be used in their pure form, because less pure materials which contain traces of growth factors and considerable quantities of mineral nutrients, are also suitable for use. When desired, there may be added to the medium mineral salts such as sodium or calcium carbonate, sodium or potassium phosphate, sodium or potassium chloride, sodium or potassium iodide, magnesium salts, copper salts, cobalt salts, and the like. If necessary, especially when the culture medium foams seriously, a defoaming agent, such as liquid paraffin, fatty oil, plant oil, mineral oil or silicone may be added.

As to the conditions for the production of cells in massive amounts, submerged aerobic cultural conditions is one method of culturing the cells. For production in small amounts, a shaking or surface culture in a flask or bottle is employed. When the growth is carried out in large tanks, vegetative forms of the organism for inoculation in the production tanks may be employed in order to avoid growth lag in the process of production. Accordingly, it is desirable first to produce a vegetative inoculum of the organism by inoculating a relatively small quantity of culture medium with spores or mycelia of the organism produced in a "slant" and culturing said inoculated medium, also called the "seed medium", and then to transfer the cultured vegetative inoculum aseptically to large tanks. The fermentation medium, in which the inoculum is produced, is generally autoclaved to sterilize the medium prior to inoculation. The pH of the medium is generally adjusted to be in the range of from about 6 to about 8 to the autoclaving step.

Agitation and aeration of the culture mixture may be accomplished in a variety of ways. Agitation may be provided by a propeller or similar mechanical agitation equipment, by revolving or shaking the fermentor or growth flask, by various pumping equipment, or by the passage of sterile air through the medium. Aeration may be effected by passing sterile air through the fermentation mixture.

The fermentation is typically conducted at a temperature in the range of from about 20 to about 30° C. (e.g., about 22° C.) for a period of from about 7 to about 21 days, which may be varied according to fermentation conditions and scales.

Preferred culturing/production media for carrying out the fermentation are those set forth in Example 1.

After growth is completed, the cells are harvested by adding the appropriate solvent, e.g. methyl ethyl ketone, to the entire culture medium and cells. If the culture is grown in a liquid fermentation, the growth could be harvested by other conventional methods, e.g., centrifugation and filtration, and then extracted with the appropriate solvent, e.g., methyl ethyl ketone.

The product of the present invention can be recovered from the culture medium by conventional means which are commonly used for the recovery of other known substances. The substances produced may be found in either or both the cultured mycelium and broth filtrate, and accordingly can be isolated and purified from the mycelium and the filtrate, which are obtained by filtering or centrifuging the cultured broth, by a conventional method such as concentration under reduced pressure, lyophilization, extraction with a conventional solvent, such as methylene chloride or methanol and the like, pH adjustment, treatment with a conventional resin (e.g., anion or cation exchange resin, non-ionic adsorption resin, etc.), treatment with a conventional adsorbent (e.g., activated charcoal, silicic acid, silica gel, cellulose, alumina, etc.), crystallization, recrystallization, and the like. A preferred method is extraction of cultured whole broth with methyl ethyl ketone, followed by filtration of the extract through filtering aid such as diatomaceous earth. The methyl ethyl ketone layer of the filtrate is separated and concentrated to dryness initially by evaporating under reduced pressure followed by lyophilization. The compounds are finally isolated either by solvent partitioning and crystallization or by preparative HPLC on reversed phase systems.

Many of the compounds of Formula (I) can be obtained by chemical modification of Compound A, using oxidation, reduction, esterification, amidation, acylation, and alkylation methods known to those of ordinary skill in the art. Schemes I and II illustrate methods for preparing representative compounds of Formula (I). Compound B can be produced by mild oxidation with sulfur trioxide-pyridine or pyridinium chlorochromate. Compound C can be obtained by oxidation with chromium trioxide or another oxidizing agent similar in strength. Forming a mixed anhydride of A followed by amidation with ammonia will afford Compound D. The reaction of compound A with diazomethane will result in Compound E. Selective acylation with acetic anhydride in the presence of organic base such as pyridine can produce compound F which, upon selective reduction with sodium borohydride, can form compound I. Sodium borohydride reduction of compound A can afford compounds G and H as well as a dihydroxy derivative.

Scheme I
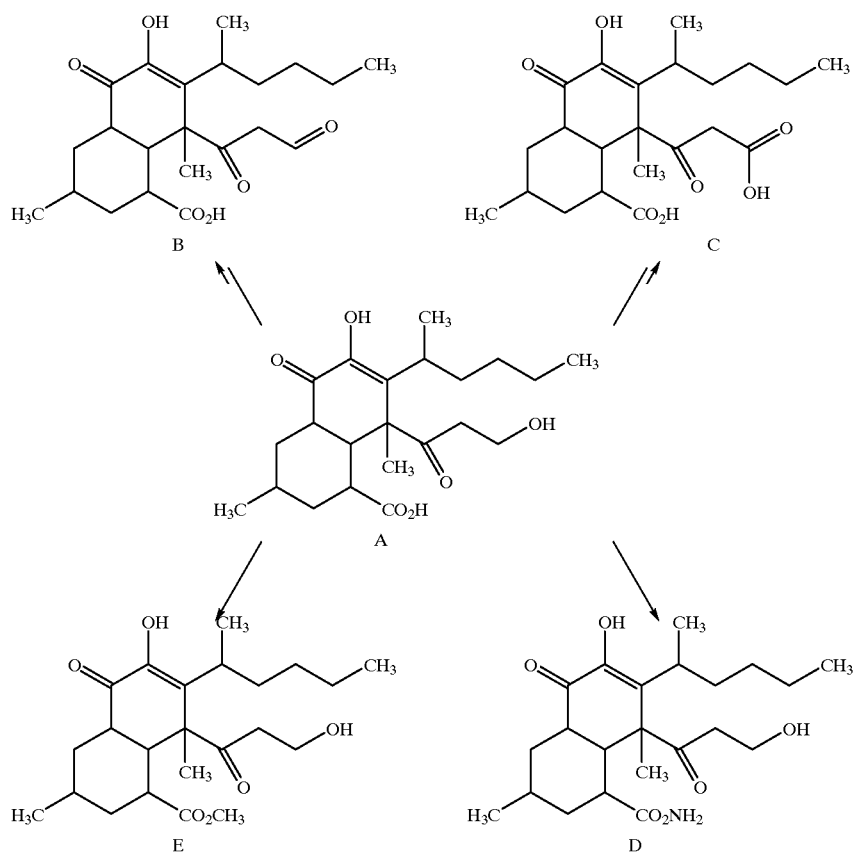
Scheme II
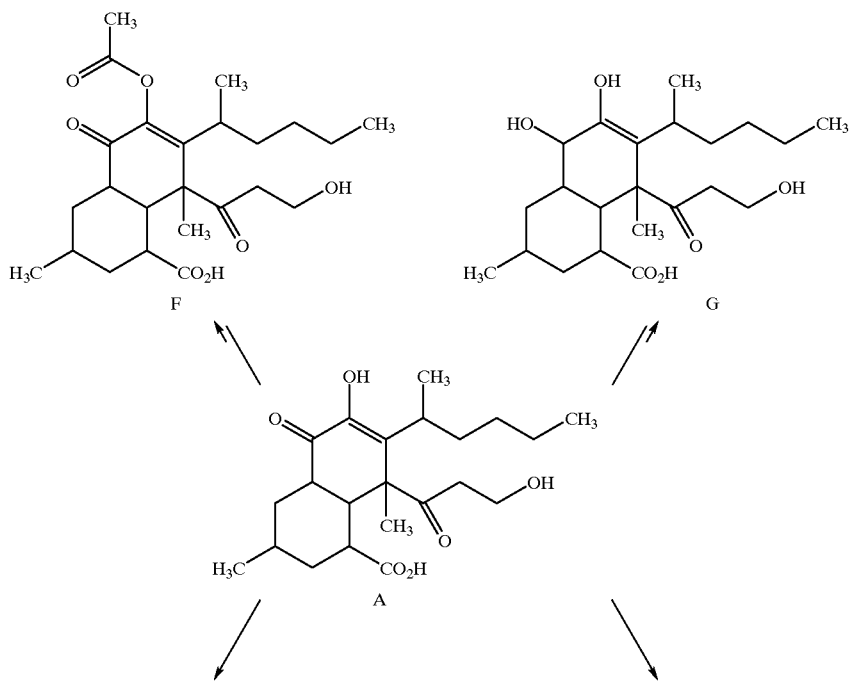

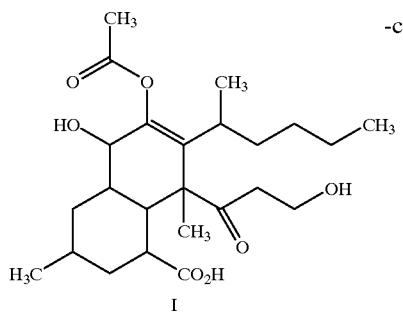 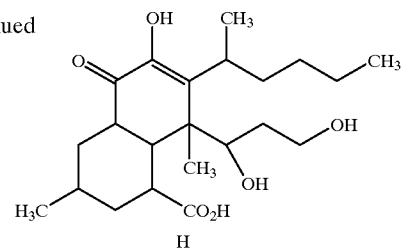

The compounds of the present invention may be administered in the form of pharmaceutically acceptable salts. The term "pharmaceutically acceptable salt" is intended to include all acceptable salts such as acetate, lactobionate, benzenesulfonate, laurate, benzoate, malate, bicarbonate, maleate, bisulfate, mandelate, bitartrate, mesylate, borate, methylbromide, bromide, methylnitrate, calcium edetate, methylsulfate, camsylate, mucate, carbonate, napsylate, chloride, nitrate, clavulanate, N-methylglucamine, citrate, ammonium salt, dihydrochloride, oleate, edetate, oxalate, edisylate, pamoate (embonate), estolate, palmitate, esylate, pantothenate, fumarate, phosphate/diphosphate, gluceptate, polygalacturonate, gluconate, salicylate, glutamate, stearate, glycollylarsanilate, sulfate, hexylresorcinate, subacetate, hydrabamine, succinate, hydrobromide, tannate, hydrochloride, tartrate, hydroxynaphthoate, teoclate, iodide, tosylate, isothionate, triethiodide, lactate, panoate, valerate, and the like which can be used as a dosage form for modifying the solubility or hydrolysis characteristics or can be used in sustained release or pro-drug formulations. Depending on the particular functionality of the compound of the present invention, pharmaceutically acceptable salts of the compounds of this invention include those formed from cations such as sodium, potassium, aluminum, calcium, lithium, magnesium, zinc, and from bases such as ammonia, ethylenediamine, N-methyl-glutamine, lysine, arginine, ornithine, choline, N,N'-dibenzylethylenediamine, chloroprocaine, diethanolamine, procaine, N-benzylphenethylamine, diethylamine, piperazine, tris (hydroxymethyl)aminomethane, and tetramethylammonium hydroxide. These salts may be prepared by standard procedures, e.g. by reacting a free acid with a suitable organic or inorganic base. Where a basic group is present, such as amino, an acidic salt, i.e. hydrochloride, hydrobromide, acetate, pamoate, trifluoroacetate, and the like, can be used as the dosage form.

Also, in the case of an acid (—COOH) or alcohol group being present, pharmaceutically acceptable esters can be employed, e.g. acetate, maleate, pivaloyloxymethyl, and the like, and those esters known in the art for modifying solubility or hydrolysis characteristics for use as sustained release or prodrug formulations.

For these purposes, the compounds of the present invention may be administered orally, parenterally (including subcutaneous injections, intravenous, intramuscular, intrasternal injection or infusion techniques), by inhalation spray, or rectally, in dosage unit formulations containing conventional non-toxic pharmaceutically-acceptable carriers, adjuvants and vehicles.

The term "administration" and variants thereof (e.g., "administering" a compound) in reference to a compound of the invention each mean providing the compound or a prodrug of the compound to the subject in need of treatment. When a compound of the invention or prodrug thereof is provided in combination with one or more other active agents (e.g., HIV/AIDS antivirals), "administration" and its variants are each understood to include concurrent and sequential provision of the compound or prodrug thereof and other agents.

The term "subject," (alternatively referred to herein as "patient") as used herein refers to an animal, typically a mammal, preferably a human, who has been the object of treatment, observation or experiment.

Thus, in accordance with the present invention there is further provided a method of treating and a pharmaceutical composition for treating HIV infection and AIDS. The treatment involves administering to a patient in need of such treatment a pharmaceutical composition comprising a pharmaceutical carrier and a therapeutically-effective amount of a compound of the present invention or one of its pharmaceutically acceptable salts.

As used herein, the term "composition" is intended to encompass a product comprising the specified ingredients in the specified amounts, as well as any product which results directly, or indirectly, from combination of the specified ingredients in the specified amounts.

The term "pharmaceutically acceptable" means that the carrier, diluent or excipient is compatible with the other ingredients of the formulation and is not deleterious to the recipient thereof.

The term "therapeutically effective amount" as used herein means that amount of active compound or pharmaceutical agent that elicits the biological or medicinal response in a tissue, system, animal or human that is being sought by a researcher, veterinarian, medical doctor or other clinician, which includes alleviation of the symptoms of the disease being treated.

These pharmaceutical compositions may be in the form of orally-administrable suspensions or tablets, nasal sprays, sterile injectable preparations, for example, as sterile injectable aqueous or oleagenous suspensions or suppositories.

When administered orally as a suspension, these compositions are prepared according to techniques well-known in the art of pharmaceutical formulation and may contain microcrystalline cellulose for imparting bulk, alginic acid or sodium alginate as a suspending agent, methylcellulose as a viscosity enhancer, and sweeteners/flavoring agents known in the art. As immediate release tablets, these compositions may contain microcrystalline cellulose, dicalcium phosphate, starch, magnesium stearate and lactose and/or other excipients, binders, extenders, disintegrants, diluents and lubricants known in the art.

When administered by nasal aerosol or inhalation, these compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

The injectible solutions or suspensions may be formulated according to known art, using suitable non-toxic, parenterally-acceptable diluents or solvents, such as mannitol, 1,3-butanediol, water, Ringer's solution or isotonic sodium chloride solution, or suitable dispersing or wetting and suspending agents, such as sterile, bland, fixed oils, including synthetic mono- or diglycerides, and fatty acids, including oleic acid.

When rectally administered in the form of suppositories, these compositions may be prepared by mixing the drug with a suitable non-initiating excipient, such as cocoa butter, synthetic glyceride esters of polyethylene glycols, which are solid at ordinary temperatures, but liquefy and/or dissolve in the rectal cavity to release the drug.

The compounds of this invention can be administered orally to humans in a dosage range of about 0.01 to about 1000 mg/kg body weight in divided doses. One preferred dosage range is from about 0.1 to about 200 mg/kg body weight orally in divided doses. Another preferred dosage range is from about 0.5 to about 100 mg/kg body weight orally in divided doses. For oral administration, the compositions are preferably provided in the form of tablets containing 1.0 to 1000 milligrams of the active ingredient, particularly 1.0, 5.0, 10.0, 15.0. 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

The present invention is also directed to combinations of the HIV integrase inhibitor compounds with one or more agents useful in the treatment of AIDS. For example, the compounds of this invention may be effectively administered, whether at periods of pre-exposure and/or post-exposure, in combination with effective amounts of the HIV/AIDS antivirals, imunomodulators, antiinfectives, or vaccines, such as those in the following table.

The present invention is also directed to combinations of the HIV protease inhibitor compounds with one or more agents useful in the treatment of HIV infection and AIDS. For example, the compounds of this invention may be effectively administered, whether at periods of pre-exposure and/or post-exposure, in combination with effective amounts of the HIV/AIDS antivirals, imunomodulators, antiinfectives, or vaccines, such as those in Table 1 as follows:

| Drug Name | Manufacturer | Indication |
|---|---|---|
| ANTIVIRALS | | |
| 097 | Hoechst/Bayer | HIV infection, AIDS, ARC (non-nucleoside reverse transcriptase inhibitor) |
| Amprenavir 141 W94 | Glaxo Wellcome | HIV infection, AIDS, ARC (protease inhibitor) |
| Abacavir GW 1592 1592U89 | Glaxo Welcome | HIV infection, AIDS, ARC (reverse transcriptase inhibitor) |
| Acemannan | Carrington Labs (Irving, TX) | ARC |
| Acyclovir | Burroughs Wellcome | HIV infection, AIDS, ARC, in combination with AZT |
| AD-439 | Tanox Biosystems | HIV infection, AIDS, ARC |
| AD-519 | Tanox Biosystems | HIV infection, AIDS, ARC |
| Adefovir dipivoxil AL-721 | Gilead Sciences Ethigen (Los Angeles, CA) | HIV infection ARC, PGL HIV positive, AIDS |
| Alpha Interferon | Glaxo Wellcome | Kaposi's sarcoma, HIV in combination w/Retrovir |
| Ansamycin LM 427 | Adria Laboratories (Dublin, OH) Erbamont (Stamford, CT) | ARC |
| Antibody which neutralizes pH labile alpha aberrant Interferon | Advanced Biotherapy Concepts (Rockville, MD) | AIDS, ARC |
| AR177 | Aronex Pharm | HIV infection, AIDS, ARC |
| beta-fluoro-ddA | Nat'l Cancer Institute | AIDS-associated diseases |
| BMS-232623 (CGP-73547) | Bristol-Myers Squibb/ Novartis | HIV infection, AIDS, ARC (protease inhibitor) |
| BMS-234475 (CGP-61755) | Bristol-Myers Squibb/ Novartis | HIV infection, AIDS, ARC (protease inhibitor) |
| CI-1012 | Warner-Lambert | HIV-1 infection |
| Cidofovir | Gilead Science | CMV retinitis, herpes, papillomavirus |
| Curdlan sulfate | AJI Pharma USA | HIV infection |
| Cytomegalovirus immune globin | MedImmune | CMV retinitis |
| Cytovene Ganciclovir | Syntex | sight threatening CMV peripheral CMV retinitis |
| Delaviridine | Pharmacia-Upjohn | HIV infection, AIDS, ARC (protease inhibitor) |
| Dextran Sulfate | Ueno Fine Chem. Ind. Ltd. (Osaka, Japan) | AIDS, ARC, HIV positive asymptomatic |
| ddC Dideoxycytidine | Hoffman-La Roche | HIV infection, AIDS, ARC |
| ddI Dideoxyinosine | Bristol-Myers Squibb | HIV infection, AIDS, ARC; combination with AZT/d4T |
| DMP-450 | AVID (Camden, NJ) | HIV infection, AIDS, ARC (protease inhibitor) |
| EL10 | Elan Corp, PLC (Gainesville, GA) | HIV infection |
| Efavirenz (DMP 266) (-) 6-Chloro-4(S)- cyclopropy- lethynyl-4(S)- trifluoro-methyl- 1,4-dihydro-2H-3, 1-benzoxazin- 2-one, | DuPont (SUSTIVA ®), Merck (STOCRIN ®) | HIV infection, AIDS, ARC (non-nucleoside RT inhibitor) |
| Famciclovir | Smith Kline | herpes zoster, herpes simplex |

-continued

| Drug Name | Manufacturer | Indication |
|---|---|---|
| FTC | Emory University | HIV infection, AIDS, ARC (reverse transcriptase inhibitor) |
| GS 840 | Gilead | HIV infection, AIDS, ARC (reverse transcriptase inhibitor) |
| HBY097 | Hoechst Marion Roussel | HIV infection, AIDS, ARC (non-nucleoside reverse transcriptase inhibitor) |
| Hypericin | VIMRx Pharm. | HIV infection, AIDS, ARC |
| Recombinant Human Interferon Beta | Triton Biosciences (Almeda, CA) | AIDS, Kaposi's sarcoma, ARC |
| Interferon alfa-n3 | Interferon Sciences | ARC, AIDS |
| Indinavir | Merck | HIV infection, AIDS, ARC, asymptomatic HIV positive, also in combination with AZT/ddI/ddC |
| Compound Q | Merck | HIV infection, AIDS, ARC, asymptomatic HIV positive |
| ISIS 2922 | ISIS Pharmaceuticals | CMV retinitis |
| KNI-272 | Nat'l Cancer Institute | HIV-assoc. diseases |
| Lamivudine, 3TC | Glaxo Wellcome | HIV infection, AIDS, ARC (reverse transcriptase inhibitor); also with AZT |
| Lobucavir | Bristol-Myers Squibb | CMV infection |
| Nelfinavir | Agouron Pharmaceuticals | HIV infection, AIDS, ARC (protease inhibitor) |
| Nevirapine | Boeheringer Ingleheim | HIV infection, AIDS, ARC (protease inhibitor) |
| Novapren | Novaferon Labs, Inc. (Akron, OH) | HIV inhibitor |
| Peptide T Octapeptide Sequence | Peninsula Labs (Belmont, CA) | AIDS |
| Trisodium Phosphonoformate | Astra Pharm. Products, Inc | CMV retinitis, HIV infection, other CMV infections |
| PNU-140690 | Pharmacia Upjohn | HIV infection, AIDS, ARC (protease inhibitor) |
| Probucol | Vyrex | HIV infection, AIDS |
| RBC-CD4 | Sheffield Med. Tech (Houston TX) | HIV infection, AIDS, ARC |
| Ritonavir | Abbott | HIV infection, AIDS, ARC (protease inhibitor) |
| Saquinavir | Hoffmann-LaRoche | HIV infection, AIDS, ARC (protease inhibitor) |
| Stavudine; d4T Didehydrodeoxythymidine | Bristol-Myers Squibb | HIV infection, AIDS, ARC |
| Valaciclovir | Glaxo Wellcome | genital HSV & CMV infections |
| Virazole Ribavirin | Viratek/ICN (Costa Mesa, CA) | asymptomatic HIV positive, LAS, ARC |
| VX-478 | Vertex | HIV infection, AIDS, ARC |
| Zalcitabine | Hoffmann-La Roche | HIV infection, AIDS, ARC, with AZT |
| Zidovudine; AZT | Glaxo Wellcome | HIV infection, AIDS, ARC, Kaposi's sarcoma, in combination with other therapies |
| ABT-378 | Abbott | HIV infection, AIDS, ARC (protease inhibitor) |

-continued

| Drug Name | Manufacturer | Indication |
|---|---|---|
| JE2147/AG1776 | Agouron | HIV infection, AIDS, ARC (protease inhibitor) |
| T-20 T-1249 | Trimeris | HIV infection, AIDS, ARC (fusion inhibitor) |
| BMS 232632 | Bristol-Myers-Squibb | HIV infection, AIDS, ARC (protease inhibitor) |
| IMMUNO-MODULATORS | | |
| AS-101 | Wyeth-Ayerst | AIDS |
| Bropirimine | Pharmacia Upjohn | advanced AIDS |
| Acemannan | Carrington Labs, Inc. (Irving, TX) | AIDS, ARC |
| CL246,738 | American Cyanamid Lederle Labs | AIDS, Kaposi's sarcoma |
| EL10 | Elan Corp, PLC (Gainesville, GA) | HIV infection |
| FP-21399 | Fuki ImmunoPharm | blocks HIV fusion with CD4 + cells |
| Gamma Interferon | Genentech | ARC, in combination w/TNF (tumor necrosis factor) |
| Granulocyte Macrophage Colony Stimulating Factor | Genetics Institute Sandoz | AIDS |
| Granulocyte Macrophage Colony Stimulating Factor | Hoeschst-Roussel Immunex | AIDS |
| Granulocyte Macrophage Colony Stimulating Factor | Schering-Plough | AIDS, combination w/AZT |
| HIV Core Particle Immunostimulant | Rorer | seropositive HIV |
| IL-2 Interleukin-2 | Cetus | AIDS, in combination w/AZT |
| IL-2 Interleukin-2 | Hoffman-La Roche Immunex | AIDS, ARC, HIV, in combination w/AZT |
| IL-2 Interleukin-2 (aldesleukin) | Chiron | AIDS, increase in CD4 cell counts |
| Immune Globulin Intravenous (human) | Cutter Biological (Berkeley, CA) | pediatric AIDS, in combination w/AZT |
| IMREG-1 | Imreg (New Orleans, LA) | AIDS, Kaposi's sarcoma, ARC, PGL |
| IMREG-2 | Imreg (New Orleans, LA) | AIDS, Kaposi's sarcoma, ARC, PGL |
| Imuthiol Diethyl Dithio Carbamate | Merieux Institute | AIDS, ARC |
| Alpha-2 Interferon | Schering Plough | Kaposi's sarcoma w/AZT, AIDS |
| Methionine-Enkephalin | TNI Pharmaceutical (Chicago, IL) | AIDS, ARC |
| MTP-PE Muramyl-Tripeptide | Ciba-Geigy Corp. | Kaposi's sarcoma |
| Granulocyte Colony Stimulating Factor | Amgen | AIDS, in combination w/AZT |
| Remune | Immune Response Corp. | immunotherapeutic |
| rCD4 Recombinant Soluble Human CD4 | Genentech | AIDS, ARC |
| rCD4-IgG hybrids | | AIDS, ARC |
| Recombinant Soluble Human CD4 | Biogen | AIDS, ARC |

-continued

| Drug Name | Manufacturer | Indication |
|---|---|---|
| Interferon Alfa 2a | Hoffman-La Roche | Kaposi's sarcoma AIDS, ARC, in combination w/AZT |
| SK & F106528 Soluble T4 | Smith Kline | HIV infection |
| Thymopentin | Immunobiology Research Institute | HIV infection |
| Tumor Necrosis Factor; TNF | Genentech | ARC, in combination w/gamma Interferon |
| etanercept | Immunex Corp (Enbrel ®) | rheumatoid arthritis |
| infliximab | Centocor (Remicade ®) | rheumatoid arthritis and Crohn's disease |
| ANTI-INFECTIVES | | |
| Clindamycin with Primaquine | Pharmacia Upjohn | PCP |
| Fluconazole | Pfizer | cryptococcal meningitis, candidiasis |
| Pastille Nystatin Pastille | Squibb Corp. | prevention of oral candidiasis |
| Ornidyl Eflornithine | Merrell Dow | PCP |
| Pentamidine Isethionate (IM & IV) | LyphoMed (Rosemont, IL) | PCP treatment |
| Trimethoprim | | antibacterial |
| Trimethoprim/ sulfa | | antibacterial |
| Piritrexim | Burroughs Wellcome | PCP treatment |
| Pentamidine isethionate for inhalation | Fisons Corporation | PCP prophylaxis |
| Spiramycin | Rhone-Poulenc | cryptosporidial diarrhea |
| Intraconazole-R51211 | Janssen Pharm. | histoplasmosis; cryptococcal meningitis |
| Trimetrexate | Warner-Lambert | PCP |
| OTHER | | |
| Daunorubicin | NeXstar, Sequus | Karposi's sarcoma |
| Recombinant Human Erythropoietin | Ortho Pharm. Corp. assoc. with AZT | severe anemia |
| Recombinant Human Growth Hormone | Serono | AIDS-related wasting, cachexia |
| Leukotriene B4 Receptor Antagonist | — | HIV infection |
| Megestrol Acetate | Bristol-Myers Squibb | treatment of anorexia assoc. w/AIDS |
| Soluble CD4 Protein and Derivatives | — | HIV infection |
| Testosterone | Alza, Smith Kline | AIDS-related wasting |
| Total Enteral Nutrition | Norwich Eaton Pharmaceuticals | diarrhea and malabsorption related to AIDS |

It will be understood that the scope of combinations of the compounds of this invention with HIV/AIDS antivirals, immunomodulators, anti-infectives or vaccines is not limited to the list in Table 1 above, but includes in principle any combination with any pharmaceutical composition useful for the treatment of AIDS.

One preferred combination is a compound of the present invention and a nucleoside inhibitor of HIV reverse transcriptase such as AZT, 3TC, ddC, or ddI. Another preferred combination is a compound of the present invention and a non-nucleoside inhibitor of HIV reverse transcriptase, such as efavirenz, and optionally a nucleoside inhibitor of HIV reverse transcriptase, such as AZT, 3TC, ddC or ddI. Still another preferred combination is any one of the foregoing combinations further comprising an additional HIV protease inhibitor such as indinavir, Compound Q, nelfinavir, ritonavir, saquinavir, amprenavir, or abacavir. A preferred additional inhibitor of HIV protease is the sulfate salt of indinavir. Other preferred additional protease inhibitors are nelfinavir and ritonavir. Still another preferred additional inhibitor of HIV protease is saquinavir which is administered in a dosage of 600 or 1200 mg tid.

Other preferred combinations include a compound of the present invention with the following (1) efavirenz, optionally with AZT and/or 3TC and/or ddI and/or ddC, and optionally with indinavir; (2) any of AZT and/or ddI and/or ddC and/or 3TC, and optionally with indinavir; (3) d4T and 3TC and/or AZT; (4) AZT and 3TC; and (5) AZT and d4T.

In such combinations the compound of the present invention and other active agents may be administered together or separately. In addition, the administration of one agent may be prior to, concurrent to, or subsequent to the administration of other agent(s). These combinations may have unexpected effects on limiting the spread and degree of infection of HIV.

Efavirenz is (−)-6-chloro-4-cyclopropylethynyl-4-trifluoromethyl-1,4-dihydro-2H-3,1-benzoxazin-2-one, also known as DMP-266 or SUSTIVA® (DuPont) or STO-CRIN® (Merck). Efavirenz and its utility as an HIV reverse transcriptase inhibitor is described in U.S. Pat. No. 5,519, 021 and in the corresponding PCT published application, WO 95/20389. Efavirenz can be synthesized by the protocol of U.S. Pat. No. 5633405. Additionally, the asymmetric synthesis of an enantiomeric benzoxazinone by a highly enantioselective acetylide addition and cyclization sequence is described in Thompson et al., Tetrahedron Letters 1995, 36: 8937–40, as well as in the PCT publication, WO 96/37457.

AZT is 3'-azido-3'-deoxythymidine, is also known as zidovudine, and is available from Burroughs-Wellcome under the tradename RETROVIR®. Stavudine is 2',3'-didehydro-3'-deoxythymidine, is also known as 2',3'-dihydro-3'-deoxythymidine and d4T, and is available from Bristol-Myers Squibb under the tradename ZERIT®. 3TC is (2R-cis)-4-Amino-1-[2-(hydroxymethyl)-1,3-oxathiolan-5-yl]-2(1H)-pyrimidinone, is also known as (−)-1-[(2R,5S)-2-(hydroxymethyl)-1,3-oxathiolan-5-yl]cytosine and lamivudine, and is available from Glaxo Wellcome under the tradename EPIVIR®. ddC is 2',3'-dideoxycytidine, is also known as zalcitabine, and is available from Hoffman LaRoche under the tradename HIVID®. ddI is 2',3'-dideoxyinosine, is also known as didanosine, and is available from Bristol-Myers-Squibb under the tradename VIDEX®. The preparation of ddC, ddI and AZT are also described in EPO 0,484,071.

Indinavir is N-(2(R)-hydroxy-1(S)-indanyl)-2(R)-phenylmethyl-4-(S)-hydroxy-5-(1-(4-(3-pyridyl-methyl)-2 (S)-N'-(t-butylcarboxamido)-piperazinyl))-pentaneamide, and can be prepared as described in U.S. Pat. No. 5,413,999. Indinavir is generally administered as the sulfate salt at a dosage of 800 mg three times a day. Indinavir is available from Merck under the tradename CRIXIVAN®.

Compound Q is N-(2(R)-hydroxy-1(S)-indanyl)-2(R)-phenylmethyl-4(S)-hydroxy-5-(1-(4-(2-benzo[b] furanylmethyl)-2(S)-N'-(t-butylcarboxamido)-piperazinyl)) pentaneamide, preferably administered as the sulfate salt. Compound Q can be prepared as described in U.S. Pat. No. 5,646,148.

Ritonavir is [5S-(5R*,8R*,10R*, 11R*)]-10-hydroxy-2-methyl-5-(1-methylethyl)-1-[2-(1-methylethyl)-4- thiazolyl]-3,6-dioxo-8,11-bis(phenylmethyl)-2,4,7,12-tetraazatridecan-13-oic acid 5-thiazolylmethyl ester, also known as 5-thiazolylmethyl [(aS)-a-[(1S,3S)-1-hydroxy-3-[(2S)-2-[3-[(2-isopropyl-4-thiazolyl)methyl]-3-methylureido]-3-methylbutyramido]-4-phenylbutyl] phenethyl]carbamate. It is available from Abbott under the tradename NORVIR®. Ritonavir can be prepared as described in U.S. Pat. No. 5,484,801.

Nelfinavir is [3S-[2(2S*,3S*),3a,4ab,8ab]]-N-(1,1-dimethylethyl)decahydro-2-[2-hydroxy-3-[(3-hydroxy-2-methylbenzoyl)amino]-4-(phenylthio)butyl]-3-isoquinolinecarboxamide monomethanesulfonate, also known as (3S,4aS,8aS)-N-tert-Butyl-2-[(2R,3R)-3-(3,2-crestoamido)-2-hydroxy-4-(phenylthio)butyl]decahydro-3-isoquinolinecarboxamide monomethanesulfonate and VIRACEPT®, which is commercially available from Agouron. Nelfinavir can be prepared as described in U.S. Pat. No. 5,484,926.

Saquinavir is N-tert-butyl-decahydro-2-[2(R)-hydroxy-4-phenyl-3(S)-[[N-(2-quinolylcarbonyl)-L-asparaginyl] amino]butyl]-(4aS,8aS)-isoquinoline-3(S)-carboxamide, also known as INVIRASE®. Saquinavir can be prepared in accordance with procedures disclosed in U.S. Pat. No. 5,196,438. INVIRASE® (saquinavir mesylate) is available from Roche Laboratories. Saquinavir can be prepared as described in U.S. Pat. No. 5,196,438.

Amprenavir is 4-amino-N-((2 syn,3S)-2-hydroxy-4-phenyl-3-((S)-tetrahydrofuran-3-yloxycarbonylamino)-butyl)-N-isobutyl-benzenesulfonamide, also known as Compound 168 and 141 W94. Amprenavir is an aspartyl protease inhibitor that can be prepared by following the procedures described in U.S. Pat. No. 5,585,397. Amprenavir is available under the tradename AGENERASE® from Glaxo Wellcome. Amprenavir can be prepared as described in U.S. Pat. No. 5,783,701.

Abacavir is (1S,4R)-cis-4-[2-amino-6-(cyclopropylamino)-9H-purin-9-yl]-2-cyclopentene-1-methanol, also known as 1592U89. Abacavir can be prepared by following the protocol of EP 0434450.

Abbreviations used in this specification include the following:

Ac=acetyl

AIDS=acquired immune deficiency syndrome

ARC=AIDS related complex

ESIMS=electron spray ionization mass spectroscopy

FABMS=fast atom bombardment mass spectroscopy

ATCC=American Type Culture Collection

FVM=frozen vegetative mycelia

HIV=human immunodeficiency virus

HPLC=high performance liquid chromatography

HR-EI MS=high resolution electron impact mass spectroscopy

Me=methyl

MEK=methyl ethyl ketone m.p.=melting point

NMR=nuclear magnetic resonance rh=relative humidity

SNY=sucrose nitrate yeast

TFA=trifluoroacetic acid

UV=ultraviolet

The following examples serve only to illustrate the invention and its practice. The examples are not to be construed as limitations on the scope or spirit of the invention.

EXAMPLE 1

Fermentation of MF 6608 (ATCC PTA-1691; F-851,192)

A. Seed

The composition of the seed medium in grams per liter (unless otherwise noted) was as follows: corn steep powder (2.5), tomato paste (40.0), oat flour (10.0), glucose (10.0), and a trace elements solution (10.0 mL/L). The trace elements solution was prepared in 0.6N HCl and had a composition in grams per liter as follows: $FeSO_4 \cdot 7H_2O$ (1.0), $MnSO_4 \cdot H_2O$ (1.0), $CuCl_2 \cdot 2H_2O$ (0.025), $CaCl_2 \cdot (0.1)$, $H_3BO_3$ (0.056), $(NH_4)_6Mo_7O_{24} \cdot 4H_2O$ (0.019), and $ZnSO_4 \cdot 7H_2O$ (0.2).

The seed medium was prepared with distilled water and the pH was adjusted to 6.8 prior to sterilization. The medium was dispensed at 50 mL/250 mL plain Erlenmeyer flask. Cotton closures were used. Sterilization was conducted at 121° C. for twenty minutes.

Frozen vials of vegetative growth of culture MF 6608 were stored in 10–20% glycerol at −75° C. The vials were thawed to room temperature and used to inoculate seed cultures, at 1.0 mL per 50 mL seed medium. The cultures were grown on a gyratory shaker (220 rpm) for 3 days at 25° C. and 85% rh, until a sufficient amount of biomass was obtained.

B. Production

B.1. Solid Production Medium

The composition of the solid substrate fermentation medium consisted of a solid portion and a liquid portion. The solid portion was 675 cc of vermiculite, which was added to a 2-liter roller bottle, which was plugged with a latex closure, autoclaved for 60 minutes, and dried for 30 minutes.

The liquid portion had a composition in grams per liter (unless otherwise noted) as follows:

| | |
|---|---|
| Glucose (added separately) | 150.0 |
| Glycerol | 20.0 |
| Yeast extract | 4.0 |
| $NaNO_3$ | 1.0 |
| Monosodium glutamate | 3.0 |
| $Na_2HPO_4$ | 0.5 |
| $MgSO_4 \cdot 7H_2O$ | 1.0 |
| K-elements | 1.0 mL/L |
| $CaCO_3$ | 8.0 |

The K-elements solution employed in the liquid portion was prepared with distilled water and had a composition in grams per liter (unless otherwise noted) as follows:

| | |
|---|---|
| $FeCl_3 \cdot 6H_2O$ | 5.8 |
| $MnSO_4 \cdot H_2O$ | 0.1 |
| $CoCl_2 \cdot 6H_2O$ | 0.02 |
| $CuSO_4 \cdot 5H_2O$ | 0.015 |
| $Na_2MoO_4 \cdot 2H_2O$ | 0.012 |
| $ZnCl_2$ | 0.02 |
| $SnCl_2 \cdot 2H_2O$ | 0.005 |
| $H_3BO_3$ | 0.01 |
| KCl | 0.02 |
| HCl (concentrated) | 2.0 mL/L |

The liquid portion was prepared with distilled water, wherein the pH was adjusted to 7.0 before adding $CaCO_3$, and then dispensed at 220 ml in 500 ml bottles and sterilized at 121° C. for 15 minutes.

An aliquot (12 ml) of each grown seed was placed into 220 ml of the liquid portion of the production medium. This was swirled vigorously to disperse the biomass. The contents were dispensed by pouring into a 2-liter roller culture vessel which contained 675 cc of steam-sterilized large-particle vermiculite. The contents of the roller bottle were shaken/mixed to insure homogeneous inoculation and coverage. The roller bottles were incubated horizontally, revolving at approximately 4 rpm on a Wheaton roller apparatus, at 22° C. and 75% rh for 18 days.

B.2. Liquid Production Media

The seed culture was also incubated in liquid media in shake flasks for 18 days at 22° C. and 75% rh, wherein an aliquot of the grown seed (1–2 mL) was added to each 250 mL plain Erlenmeyer flask containing 50 mL of the liquid media. Two liquid media were employed. Medium I had the following composition in grams/liter:

| Glucose | 10.0 |
|---|---|
| Fructose | 15.0 |
| Sucrose | 40.0 |
| Casamino acids | 2.0 |
| Asparagine | 2.0 |
| Yeast extract | 1.0 |
| $Na_2HPO_4$ | 0.5 |
| $MgSO_4 \cdot 7H_2O$ | 1.0 |
| $CaCl_2$ | 0.5 |
| K-elements | 1.0 ml/L |

Medium II had the following composition in grams/liter:

| Sucrose | 60.0 |
|---|---|
| Glucose | 80.0 |
| Glycerol | 60.0 |
| Tomato paste | 5.0 |
| Ardamine PH | 5.0 |
| $(NH_4)_2SO_4$ | 2.0 |
| $MgSO_4 \cdot 7H_2O$ | 0.5 |
| $CaCl_2$ | 0.5 |
| K-elements | 1.0 ml/L |

Each of the media was prepared with distilled water with pH adjusted to 7.0, dispensed in amounts of 50 mL per 250 ml plain Erlenmeyer flask, and then sterilized at 121° C. for 15–20 minutes.

The production culture resulting from B.1. was worked up as described in Example 2.

EXAMPLE 2
Isolation of Compound A

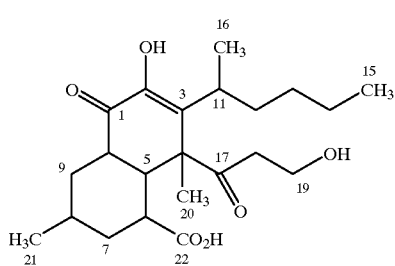
Compound A

The fermentation broth (30 mL) was extracted with methyl ethyl ketone (MEK) and filtered through celite. MEK was removed from the extract under reduced pressure and the solid residue was chromatographed on a column filled with sephadex LH-20 and eluted with methanol. The single active cut obtained was further purified by HPLC (Zorbax RX C8 column 22.4×250 mm, ACN/Water 50:50 with 0.1% TFA, flow rate 8 ml/min) to elute an active major peak at tR=25 min. The residue of the active fraction was recrystallized from nitromethane to produce 8 mg of colorless fine needles of Compound A.

m.p. 198–202° C.

HR-FTMS m/z 395.2436 [M+H].

IR 2950, 2871, 1699 (C=O), 1666 (C=O), 1639 (C=O), 1460, 1383, 1178, 1027 $cm^{-1}$.

UV (MeOH)$\lambda_{max}$=275 nm ($\epsilon$=24882).

$[\alpha]^{25}_D$ (MeOH)+69.5°(c 0.2).

$^1H$ and $^{13}C$ NMR Assignment of Compound A in pyridine $d_5$

| Position | δC | δH |
|---|---|---|
| 1 | 195.0 | |
| 2 | 146.4 | |
| 3 | 137.9 | |
| 4 | 58.5 | |
| 5 | 42.8 | 2.9 (brt, 11.0) |
| 6 | 47.6 | 2.8 (dt, 3.0, 12.5) |
| 7 | 40.0 | 1.3, 2.0 (m) |
| 8 | 30.8 | 1.3 (m) |
| 9 | 35.1 | 1.1, 2.6 (m) |
| 10 | 43.3 | 2.4 (brt, 8.5) |
| 11 | 34.7 | 1.8 (m) |
| 12 | 36.4 | 1.8, 2.5 (m) |
| 13 | 31.4 | 1.2 (m) |
| 14 | 23.4 | 1.3 (m) |
| 15 | 14.4 | 0.8 (t, 7.0) |
| 16 | 18.4 | 1.4 (s) |
| 17 | 211 | |
| 18 | 42.1 | 3.2, 3.9 (m) |
| 19 | 58.1 | 4.3, 4.4 (m) |
| 20 | 14.7 | 1.67 (s) |
| 21 | 22.2 | 0.9 (d, 5.5) |
| 22 | 177.5 | |

EXAMPLE 3

HIV Integrase Assay: Strand Transfer Catalyzed by Recombinant Integrase and Preintegration Complexes Assays for the strand transfer activity of integrase can be conducted according to Wolfe et al., *J. Virol.* 1996, 70: 1424 and Farnet and Bushman, *Cell* 1997, 88: 483 for recombinant integrase and preintegration complexes, respectively, hereby incorporated by reference. Compound A was tested in the recombinant integrase assay and found to have an $IC_{50}$ of about 20 micromolar.

EXAMPLE 4

Oral Composition

As a specific embodiment of an oral composition of a compound of this invention, 50 mg of Compound A is combined with sufficient finely divided lactose to provide a total amount of 580 to 590 mg to fill a size 0 hard gelatin capsule.

While the foregoing specification teaches the principles of the present invention, with examples provided for the purpose of illustration, the practice of the invention encompasses all of the usual variations, adaptations and/or modifications that come within the scope of the following claims.

What is claimed:

1. A compound of Formula (I):

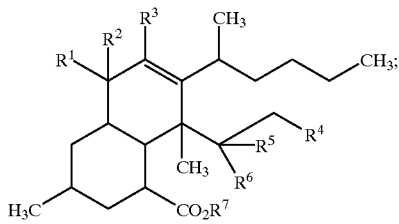
(I)

wherein
one of $R^1$ and $R^2$ is —H, and the other of $R^1$ and $R^2$ is —OH; or $R^1$ and $R^2$ together form oxo;
$R^3$ is —OH, —OC(O)CH$_3$ or —OR$^a$;
$R^4$ is —CH$_2$OH, —CH$_2$OC(O)CH$_3$, —CHO, or —CO$_2$H;
one of $R^5$ and $R^6$ is —H, and the other of $R^5$ and $R^6$ is —OH; or $R^5$ and $R^6$ together form oxo;
$R^7$ is —H, —R$^a$, —NH$_2$, or —NR$^a$R$^b$;
each $R^a$ is independently —C$_1$–C$_4$ alkyl; and
$R^b$ is —H or —C$_1$–C$_4$ alkyl;
or a pharmaceutically acceptable salt thereof.

2. The compound according to claim 1, which is a compound of Formula (II):

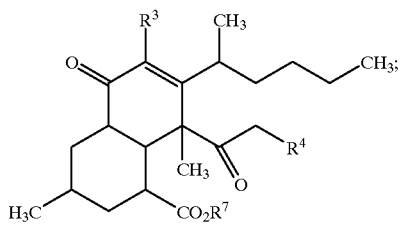
(II)

or a pharmaceutically acceptable salt thereof.

3. The compound according to claim 2, wherein
$R^3$ is —OH; and
$R^4$ is —CH$_2$OH;
or a pharmaceutically acceptable salt thereof.

4. The compound according to claim 1, which is Compound A of formula:

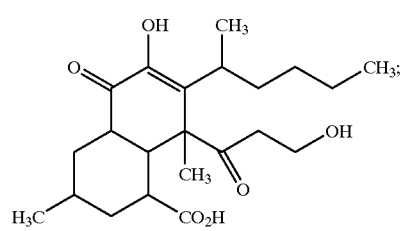
A or a pharmaceutically acceptable salt thereof.

5. A pharmaceutical composition comprising a therapeutically effective amount of a compound according to claim 1, or a pharmaceutically acceptable salt thereof, and a pharmaceutically acceptable carrier.

6. The pharmaceutical composition according to claim 5, wherein the compound is Compound A:

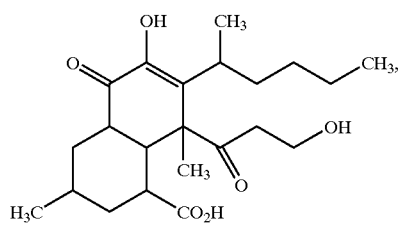
A or a pharmaceutically acceptable salt thereof.

7. The pharmaceutical composition of claim 5, further comprising a therapeutically effective amount of an agent for treating HIV infection or AIDS selected from (a) an HIV/AIDS antiviral agent, (b) an immunomodulator, and (c) an anti-infective agent.

8. The pharmaceutical composition according to claim 7 wherein the HIV/AIDS antiviral agent is indinavir, or a pharmaceutically acceptable salt thereof.

9. A pharmaceutical composition comprising a combination of a therapeutically effective amount of a compound of claim 1, or a pharmaceutically acceptable salt thereof, and a therapeutically effective amount of an agent for treating HIV infection or AIDS selected from (a) an HIV/AIDS antiviral agent, (b) an immunomodulator, and (c) an anti-infective agent.

10. A pharmaceutical composition made by combining the compound of claim 1, or a pharmaceutically acceptable salt thereof, and a pharmaceutically acceptable carrier.

11. A process for making a pharmaceutical composition which comprises combining a compound of claim 1, or a pharmaceutically acceptable salt thereof, and a pharmaceutically acceptable carrier.

12. A method of inhibiting HIV integrase, which comprises administering to a mammal in need of such inhibition a therapeutically effective amount of a compound according to claim 1, or a pharmaceutically acceptable salt thereof.

13. A method of treating infection by HIV, or of treating AIDS or ARC, which comprises administering to a mammal in need of such treatment a therapeutically effective amount of a compound according to claim 1, or a pharmaceutically acceptable salt thereof.

14. The method according to claim 13, which further comprises administering a therapeutically effective amount of another agent for treating HIV infection or AIDS selected from selected from (a) an HIV/AIDS antiviral agent, (b) an immunomodulator, and (c) an anti-infective agent.

15. The method according to claim 14, wherein the HIV/AIDS antiviral agent is indinavir, or a pharmaceutically acceptable salt thereof.

* * * * *